United States Patent [19]

Cooper et al.

[11] Patent Number: 5,556,782
[45] Date of Patent: Sep. 17, 1996

[54] TRANSFORMED MAMMALIAN CELLS CAPABLE OF EXPRESSING CECROPIN B

[75] Inventors: Richard K. Cooper; Frederick M. Enright, both of Baton Rouge, La.

[73] Assignee: Board of Supervisors of Louisiana State University and Agricultural & Mechanical College, Baton Rouge, La.

[21] Appl. No.: 450,252

[22] Filed: May 25, 1995

Related U.S. Application Data

[63] Continuation of Ser. No. 85,282, Jun. 30, 1993, abandoned.

[51] Int. Cl.$^6$ .............................. C12N 5/10; C12N 15/85
[52] U.S. Cl. .................... 435/240.2; 435/240.21; 435/172.3; 435/320.1; 435/252.3; 536/23.1; 536/23.5; 935/9; 935/10; 935/11; 935/22; 935/29; 935/24; 935/34; 935/70; 935/71; 935/72; 935/73
[58] Field of Search ........................... 435/240.2, 240.21, 435/320.1, 252.3, 252.33; 536/23.1, 23.5; 935/9, 10, 11, 22, 29, 24, 34, 70, 71, 72–73

[56] References Cited

U.S. PATENT DOCUMENTS

| 5,028,530 | 7/1991 | Lai et al. | 435/69.1 |
| 5,206,154 | 4/1993 | Lai et al. | 435/69.7 |

FOREIGN PATENT DOCUMENTS

| 8900199 | 1/1990 | WIPO . |
| 9012866 | 11/1990 | WIPO . |

OTHER PUBLICATIONS

Klysten etal. 1990 EmBO J. 9, 217–224.
Pelham etal. 1982. "DNA Sequences Required for Transcriptional regulation of the Drosophila hsp 70 Heat Shock 9 cm in Monkey Cells and Xenopus Oocytes", in: (Schlessinger etal. eds.). *Heat Shock. From Bacteria to Man,* Cold Spring Harbor Laboratory, Cold Spring Harbor, NY. pp. 43–48.
Asubel etal. 1988. in: *Cumont Protocols in Molecular Biology.,* Greene Publ. Assoc. & Wiley Inter Sci. (John Wiley & Sons). New York, pp. 9.0.3–9.0.4.

Xanthopoulas et al., "The structure of the gene for cecropin B, an antibacterial immune protein from *Hyalophora cecropia,*" Eur. J. Biochem., vol. 172, pp. 371–376 (1988).
Kaling et al., "Liver–Specific Gene Expression: A–Activator–Binding Site, a Promoter Module Present in Vitellogen and Acute–Phase Genes," Mol. Cell. Biol., vol. 11, pp. 93–101 (1991).
Boman et al., "Cell–free immunity in Cecropia," Eur. J. Biochem., vol. 201, pp. 23–31 (1991).
Beck et al., "Invertebrate Cytokines III: Invertebrate Interleukin–1–like Molecules Stimulate Phagocytosis by Tunicate and Echinoderm Cells," Cellular Immunology, vol. 146, pp. 284–299 (1993).
Caput et al., "Identification of a common nucleotide sequence in the 3'–untranslated region of mRNA molecules specifying inflammatory mediators," Proc. Natl. Acad. Sci. USA, vol. 83, pp. 1670–1674 (1986).

*Primary Examiner*—Christopher S. F. Low
*Attorney, Agent, or Firm*—John H. Runnels

[57] ABSTRACT

Novel means have been discovered for increasing the resistance of a mammalian host (including humans) to diseases caused by intracellular bacteria, protozoa, and viruses. Novel means have also been found for treating tumors. Augmentation of the host's defenses against infectious diseases or tumors is achieved by "arming" the host's cells with a gene encoding the lytic peptide cecropin B. The host's own leukocytes, other cells involved in resistance to infection, or other cells are transformed, and expression of the gene is induced when needed to combat pathogens. Transfection of hematopoietic stem cells with the cecropin B gene will enhance disease resistance in mammals; and transfection of TIL (tumor infiltrating lymphocytes) cells or other cells can be used in the treatment of tumors. The transformed cells have the ability to produce and secrete a broad spectrum chemotherapeutic agent which has a systemic effect on certain pathogens, particularly pathogens that might otherwise evade or overcome host defenses. The peptide's expression is preferably induced only in areas of infection, where it will most effectively augment the host's defense systems. Expression of the exogenous gene does not damage a healthy recipient cell.

8 Claims, No Drawings

TRANSFORMED MAMMALIAN CELLS CAPABLE OF EXPRESSING CECROPIN B

This application is a continuation of application Ser. No. 08/085,282, filed Jun. 30, 1993 now abandoned.

This invention pertains to transformed mammalian cells capable of expressing the lytic peptide cecropin B, and uses for such cells.

INTRODUCTION

Few effective treatments exist for either acute or chronic intracellular bacterial, protozoal, or viral diseases of animals or humans. In many such infections, the infectious agent is localized within host cells. Due to the intracellular location of the infectious agents, the host immune system is often ineffective. Likewise, anti-pathogenic compounds are often ineffective, due to their difficulty in crossing host cell membranes.

Beck et al., "Invertebrate Cytokines III: Invertebrate Interleukin-1-like Molecules Stimulate Phagocytesis by Tunicate and Echinoderm Cells," Cellular Immunology, vol. 146, pp. 284–299 (1993) discusses relationships among phagocytosis mechanisms of different phyla.

Lytic Peptides

Lytic peptides are small, basic proteins. Native lytic peptides appear to be major components of the antimicrobial defense systems of a number of animal species, including those of insects, amphibians, and mammals. They typically comprise 23–39 amino acids, and have the potential for forming amphipathic alpha-helices. See Boman et al., "Humoral immunity in Cecropia pupae," Curr. Top. Microbiol. Immunol. vol. 94/95, pp. 75–91 (1981); Boman et al., "Cell-free immunity in insects," Annu. Rev. Microbiol., vol. 41, pp. 103–126 (1987); Zasloff, "Magainins, a class of antimicrobial peptides from Xenopus skin: isolation, characterization of two active forms, and partial DNA sequence of a precursor," Proc. Natl. Acad. Sci. USA, vol. 84, pp. 3628–3632 (1987); Ganz et al., "Defensins natural peptide antibiotics of human neutrophils," J. Clin. Invest., vol. 76, pp. 1427–1435 (1985); and Lee et al., "Antibacterial peptides from pig intestine: isolation of a mammalian cecropin," Proc. Natl. Acad. Sci. USA, vol. 86, pp. 9159–9162 (1989).

Lytic peptides typically have a broad spectrum of activity (e.g., against gram negative bacteria, fungi, protozoa, and viruses). Their activity is both direct and indirect (e.g., virus-infected cells are destroyed, disrupting virus production). Thus some pathogens that have developed the ability to avoid host defenses are nevertheless susceptible to destruction by lytic peptides.

At least four families of naturally-occurring lytic peptides have been discovered in the last decade: cecropins, defensins, sarcotoxins, and magainins. Boman and coworkers in Sweden performed the original work on the humoral defense system of *Hyalphora cecropia,* the giant silk moth, to protect itself from bacterial infection. See Hultmark et al., "Insect immunity. Purification of three inducible bactericidal proteins from hemolymph of immunized pupae of *Hyalphora cecropia,*" Eur. J. Biochem., vol. 106, pp. 7–16 (1980); and Hultmark et al., "Insect immunity. Isolation and structure of cecropin D. and four minor antibacterial components from cecropia pupae," Eur. J. Biochem., vol. 127, pp. 207–217 (1982).

Infection of *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence which will form an amphipathic alpha-helix. Andrequ et al., "N-terminal analogues of cecropin A: synthesis, antibacterial activity, and conformational properties," Biochem., vol. 24, pp. 1683–1688 (1985). The carboxy-terminal half of the peptide comprises a hydrophobic tail. See also Boman et al., "Cell-free immunity in Cecropia," Eur. J. Biochem., vol. 201, pp. 23–31 (1991).

Recently, a cecropin-like peptide has been isolated from porcine intestine. Lee et al., "Antibacterial peptides from pig intestine: isolation of a mammalian cecropin," Proc. Natl. Acad. Sci. USA, vol. 86, pp. 9159–9162 (1989).

Cecropin peptides have been observed to kill a number of animal pathogens other than bacteria. See Jaynes et al., "In Vitro Cytocidal Effect of Novel Lytic Peptides on *Plasmodium falciparum* and *Trypanosoma cruzi,*" FASEB, 2878–2883 (1988); Arrowood et al., "Hemolytic properties of lytic peptides active against the sporozoites of *Cryptosporidium parvus,*" J. Protozool., vol. 38, No. 6, pp. 161S–163S (1991); and Arrowood et al., "In vitro activities of lytic peptides against the sporozoites of *Cryptosporidium parvum,*" Antimicrob. Agents Chemother., vol. 35, pp. 224–227 (1991). However, normal mammalian cells do not appear to be adversely affected by cecropins, even at high concentrations. See Jaynes et al., "In vitro effect of lytic peptides on normal and transformed mammalian cell lines," Peptide Research, vol. 2, No. 2, pp. 1–5 (1989); and Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992).

Defensins, originally found in mammals, are small peptides containing six to eight cysteine residues. Ganz et al., "Defensins natural peptide antibiotics of human neutrophils," J. Clin. Invest., vol. 76, pp. 1427–1435 (1985). Extracts from normal human neutrophils contain three defensin peptides: human neutrophil peptides HNP-1, HNP-2, and HNP-3. Defensin peptides have also been described in insects and higher plants. Dimarcq et al., "Insect immunity: expression of the two major inducible antibacterial peptides, defensin and diptericin, in *Phormia terranvae,*" EMBO J., vol. 9, pp. 2507–2515 (1990); Fisher et al., Proc. Natl. Acad. Sci. USA, vol. 84, pp. 3628–3632 (1987).

Slightly larger peptides called sarcotoxins have been purified from the fleshfly *Sarcophaga peregrina.* Okada et al., "Primary structure of sarcotoxin I, an antibacterial protein induced in the hemolymph of *Sarcophaga peregrina* (flesh fly) larvae," J. Biol. Chem., vol. 260, pp. 7174–7177 (1985). Although highly divergent from the cecropins and defensins, the sarcotoxins presumably have a similar antibiotic function.

Other lytic peptides have recently been found in amphibians. Gibson and collaborators isolated two peptides from the African clawed frog, *Xenopus laevis,* peptides which they named PGS and Gly$^{10}$Lys$^{22}$PGS. Gibson et al., "Novel peptide fragments originating from PGL$_a$ and the caervlein and xenopsin precursors from *Xenopus laevis,*" J. Biol. Chem., vol. 261, pp. 5341–5349 (1986); and Givannini et al., "Biosynthesis and degradation of peptides derived from

*Xenopus laevis* prohormones," Biochem. J., vol. 243, pp. 113–120 (1987). Zasloff showed that the Xenopus-derived peptides have potent antimicrobial activity, and renamed them magainins. Zasloff, "Magainins, a class of antimicrobial peptides from Xenous skin: isolation, characterization of two active forms, and partial DNA sequence of a precursor," Proc. Natl. Acad. Sci. USA, vol. 84, pp. 3628–3632 (1987).

Synthesis of nonhomologous analogs of different classes of lytic peptides has revealed that a positively charged, amphipathic sequence containing at least 20 amino acids appears to be a requirement for lytic activity. Shiba et al., "Structure-activity relationship of Lepidopteran, a self-defense peptide of *Bombyx mori,*" Tetrahedron, vol. 44, No. 3, pp. 787–803 (1988); and unpublished data from our laboratory. A 20-mer appears to possess roughly the minimum alpha-helix length needed to span a cell membrane. Smaller peptides (or lower concentrations of peptide) not only fail to kill cells, but actually stimulate cell growth. Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992); and unpublished data from our laboratory.

Cecropins have been shown to target pathogens or compromised cells selectively, without affecting normal host cells. See Jaynes et al., "In vitro effect of lytic peptides on normal and transformed mammalian cell lines," Peptide Research, vol. 2, No. 2, pp. 1–5 (1989); Wood et al., "Toxicity of a Novel Antimicrobial Agent to Cattle and Hamster cells In vitro," Proc. Ann. Amer. Soc. Anim. Sci., Utah State University, Logan, UT. J. Anim. Sci. (Suppl. 1), vol. 65, p. 380 (1987); Arrowood et al., "Hemolytic properties of lytic peptides active against the sporozoites of *Cryptosporidium parvum,*" J. Protozool., vol. 38, No. 6, pp. 161S–163S (1991); Arrowood et al., "In vitro activities of lytic peptides against the sporozoites of *Cryptosporidium parvum,*" Antimicrob. Agents Chemother., vol. 35, pp. 224–227 (1991); and Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992).

Also of interest are the following commonly-assigned patent applications: Jaynes et al., "Method for Introduction of Disease and Pest Resistance Into Plants and Novel Genes Incorporated Into Plants Which Code Therefor," U.S. patent application Ser. No. 07/373,623, filed Jun. 29, 1989; Jaynes et al., "Plants Genetically Enhanced for Disease Resistance," U.S. patent application Ser. No. 07/646,449, filed Jan. 25, 1991; Jaynes et al., "Therapeutic Antimicrobial Polypeptides, Their Use and Methods for Preparation," U.S. patent application Ser. No. 07/069,653, filed Jul. 6, 1987; Jaynes et al., "Inhibition of Eucaryotic Pathogens and Neoplasms and Stimulation of Fibroblasts and Lymphocytes with Lyric Peptides," U.S. patent application Ser. No. 07/102,175, filed Sep. 29, 1987; and Jaynes, "Lytic Peptides: Their Use in the Treatment of Microbial Infections, Cancer and in the Promotion of Growth," U.S. patent application Ser. No. 07/336,181, filed Apr. 10, 1989.

It is believed (without wishing to be bound by this theory) that lytic peptides act by disrupting cell membranes, and that their mechanism of action relies on the ability of normal host cells to repair the resulting membrane damage. By contrast, bacteria, protozoa, and compromised host cells are unable (or less able) to repair damaged membranes. Because parasitized cells have a diminished capacity to repair membranes, after a lytic peptide "attack" they are preferentially destroyed, while adjacent normal cells repair their membranes and survive.

At least three modes have been proposed for the lytic peptide-membrane interaction which leads to cytolysis: (1) The amphipathic helix is located on the membrane surface, and the presence of the helix in the head group region disorders the lipid bilayer. Dawson et al., "The interaction of bee melittin with lipid bilayer membranes," Biochem. Biophys. Acta., vol. 510, pp. 75–86 (1978). (2) Peptide oligomers form ion channels in the membrane, resulting in osmotically-induced lysis. Tosteson et al., "The sting–melittin forms channels in lipid bilayers," Biophys. J., vol. 36, pp. 109–116 (1981). (3) The lytic peptide causes aggregation of native membrane proteins, resulting in the formation of channels or pores. Burr et al., "Role of membrane proteins in monosodium urate crystal-membrane interactions. I. Effect of pretreatment of erythrocyte neuraminidase," J. Rheumatol., vol. 17, pp. 1353–1358 (1990).

Many intracellular obligate pathogens live inside host cells because they are vulnerable to host defenses when outside the cell, where they may be destroyed by humoral or cellular defenses, or by conventional therapeutic agents. Also, known viruses and intracellular protozoa require a staging development within a host cell before becoming infectious; if released prematurely they will not be infective. Evidence indicates that the infective stages in bacterial, fungal, and protozoal pathogens are directly destroyed by lytic peptides following their release. See Jaynes et al., "In vitro effect of lytic peptides on normal and transformed mammalian cell lines," Peptide Research, vol. 2, No. 2, pp. 1–5 (1989); Jaynes et al., "In Vitro Cytocidal Effect of Novel Lyric Peptides on *Plasmodium falciparum* and *Trypanosoma cruzi,*" FASEB, 2878–2883 (1988); Arrowood et al., "Hemolytic properties of lytic peptides active against the sporozoites of *Cryptosporidium parvum,*" J. Protozool., vol. 38, No. 6, pp. 161S–163S (1991); and Arrowood et al., "In vitro activities of lytic peptides against the sporozoites of *Cryptosporidium parvum,*" Antimicrob. Agents Chemother., vol. 35, pp. 224–227 (1991).

Plants Transformed with Lytic Peptide Genes

A number of synthetic lytic peptides have been synthesized, retaining some properties of native lytic peptides. For example, Shiva I was designed as a substitution analog of native Cecropin B, having 46% homology to the natural Cecropin B molecule. However, the hydrophobic properties and charge density of the native structure were conserved in the synthetic peptide. Data supporting the ability of the Shiva I gene to enhance disease resistance has been obtained from transgenic plants. Genes encoding synthetic lytic peptides were chemically synthesized and cloned into the binary vector pBI121. For the less active peptide SB-37 (a cecropin analog), expression was controlled by a constitutive promoter, the 35S cauliflower mosaic virus 5' region-nopaline synthetase-3' polyadenylation cassette (Rogers et al., "Improved vectors for plant transformation: expression cassette vectors and new selectable markers," Meth. Enz. vol. 153, pp. 253–305 (1987)). For the more active Shiva I, expression was controlled by the wound-inducible plant promoter for proteinase inhibitor II (PiII) (Sanchez-Serrano et al., "Wound-induced expression of a potato proteinase inhibitor II gene in transgenic tobacco plants," EMBO J. vol. 6, pp. 303–306 (1987); Jaynes et al., "Expression of a cecropin B lytic peptide analog in transgenic tobacco confers enhanced resistance to bacterial wilt caused by

*Pseudomonas solanacearum,"* to appear in Plant Science (1993).

In non-wounded potato plants, PiII accumulates in the tubers, with non-detectable levels of the protein in leaves, stem or roots. When the leaves are wounded, however, expression of the gene is induced not only in the wounded leaves, but also in non-wounded upper and lower leaves and in the upper part of the stem. Pena-Cortes et al., "Systemic induction of proteinase-inhibitor-II gene expression into potato plants by wounding," Planta, vol. 174, pp. 84–91 (1988).

Transgenic tobacco plants with genes coding for lytic peptides have also been obtained via Agrobacterium transformation. Bioassays testing the disease resistance of $F_1$ progeny indicated that, compared to transgenic controls and SB-37 plants, Shiva-containing tobacco seedlings exhibited delayed wilt symptoms and reduced disease severity and mortality after infection with a highly virulent strain of *Pseudomonas solanacearum.* (*P. solanacearum* is a vascular pathogen that causes severe wilting.) Jaynes et al., "Expression of a cecropin B lytic peptide analog in transgenic tobacco confers enhanced resistance to bacterial wilt caused by *Pseudomonas solanacearum,"* to appear in Plant Science (1993). No enhanced resistance was observed for the plants producing the synthetic peptide SB-37, presumably because of its low bioactivity against this pathogen. Destefano-Beltran et al., Mol. Biol. of the Potato, pp. 205–221 (1990).

In contrast to this work in plants, to the knowledge of the inventors, no previous work has resulted in the successful expression of exogenous cecropin B in mammalian cells. In fact, very few non-mammalian genes have ever been stably expressed in a mammalian cell.

BRIEF DESCRIPTION OF SELECTED FEATURES OF THE INVENTION

Novel means have been discovered for increasing the resistance of a mammalian host (including humans) to diseases caused by intracellular bacteria, protozoa, and viruses. The infection treated may, for example, be equine infectious anemia, or infection by the human immunodeficiency virus. Novel means have also been found for treating tumors.

Augmentation of the host's defenses against infectious diseases or tumors is achieved by "arming" the host's cells with an exogenous gene for native cecropin B. The cells thus transformed may be the host's own leukocytes, other cells involved in resistance to infection, or other cells. The expression of the gene is induced when needed to combat pathogens.

For example, the transfection of hematopoietic stem cells can enhance disease resistance in mammals; and transfection of TIL (tumor infiltrating lymphocytes) cells or other cells can be used in the treatment of tumors.

It has been discovered that the gene coding for native cecropin B can be transferred and stably expressed in mammalian cells. The transformed cells have the ability to produce and secrete a broad spectrum chemotherapeutic agent which has a systemic effect on certain pathogens, particularly pathogens that might otherwise evade or overcome host defenses. The peptide's expression is preferably induced only in areas of infection, where it will most effectively augment the host's defense systems. It has been observed that expression of the exogenous gene does not damage a healthy recipient cell.

DETAILED DESCRIPTION OF THE INVENTION

General

Studies in our laboratory have shown that a variety of treatments make cells susceptible to at least some lytic peptides, in situations where corresponding untreated cells are resistant to the peptides. Resistant cells can be made susceptible by treatment with cytoskeletal inhibitors, cytochalasin D and colchicine, or by chilling the cells to 4° C. for 15 minutes prior to exposure to peptide. Resistant cells treated with trypsin also became extremely susceptible to lysis by the lytic peptides. A common factor in each of these examples of induced susceptibility appears to be an altered plasma membrane and/or cytoskeleton. The alteration may interfere with the repair of damaged membrane by hampering endocytosis or exocytosis.

Further evidence of the selective susceptibility of macrophages to the lytic peptides was obtained in a series of experiments using mouse peritoneal macrophages and *Listeria monocytogenes,* an obligate intracellular, gram-positive bacterium. Normal, non-activated, resident peritoneal macrophages (R1); and activated macrophages derived from the peritoneal cavities of Listeria-immune mice inoculated intra-peritoneally 17 hours earlier with Listeria (L1) were exposed in vitro to Listeria and then treated with a lytic peptide. Additionally, resident macrophages from normal non-Listeria immune mice were infected in vitro with Listeria (L2) and treated with the Shiva I peptide. The Shiva peptide had little effect on control resident macrophages (R1). Neither Listeria alone nor the peptide alone (without Listeria infection) resulted in significant cell death. However, Listeria-infected macrophages (L1 and L2) were killed by the peptide. Macrophages from Listeria-immune mice (L1) re-exposed to Listeria by intraperitoneal inoculation 17 hours earlier were killed when exposed to the peptide. The presence of intracellular Listeria was confirmed by microscopic examination of the groups of cells prior to treatment.

As described in greater detail below, we have developed a construct carrying the gene for the native cecropin B peptide which can be inducibly expressed in mammalian cells. This result is unexpected, particularly because the native insect promoter was able to regulate expression of the gene in mammalian cells.

The plasmid construct designated "pCEP" carries the native cecropin promoter and the native cecropin gene. Electroporation of the pCEP construct into fetal donkey dermal cells ("FDD cells") resulted in the expression of antibacterial substances when those cells were co-cultured with viable *E. coli.* This antibacterial activity was not observed in control electroporated FDD cells.

Transformation of Fetal Donkey Dermal Cells

Fetal donkey dermal cells were chosen as a model system for cecropin expression. This cell line was chosen for several reasons. First, it was known from prior studies that these cells are resistant to lysis by lytic peptides. Second, this cell line had previously been used to study the antiviral activity of several lytic peptides against Equine Infectious Anemia (EIA) infection. The EIA-infected cells were lysed by the peptides, while uninfected cells were not. The cell line has been demonstrated to be refractory to damage from electroporation. Finally, these cells will act as hosts in vitro for *Listeria monocytogens* and *T. cruzi,* agents to be used to evaluate the antimicrobial activity of the transformed cells.

FDD cells were cultivated in Eagle's minimum essential medium (MEM), supplemented with Earle's salts, L-glutamine, nonessential amino acids, 5% fetal bovine serum (FBS), and the antibiotics penicillin (100 unit/mL) and streptomycin (100 µg/mL). Cells were split once a week until the desired number were obtained. Conditioned medium which had been clarified from a freshly split culture of FDD cells after 24 hours of culture was used to maintain the cells after electroporation.

Prior to electroporation, FDD cells were rinsed with phosphate buffered saline (PBS), scraped from the flask, rinsed again with PBS, and counted. The concentration of cells was adjusted to $9\times10^5$ cells/100 µL, and the cells were placed in a BioRad 0.4 cm (electrode gap width) electroporation cuvette. To this cuvette were also added 400 µL of PBS and 1.4 µg of linearized pCEP DNA. The cuvette and its contents were kept on ice until electroporation. The cells were electroporated at 2.0 KV and 1 µF in the presence of 10 mM IPTG. Immediately after electroporation, 0.5 mL of conditioned medium was added to the cells, which were then incubated on ice for a 10 min recovery period. The cells were then transferred to flasks containing equal parts of conditioned medium and fresh medium, and were allowed to form a monolayer. Monolayered cells were trypsinized, subpassaged in 24-well plates, and allowed to form a monolayer. These cells were then subpassaged into 96-well plates. In the 96-well plates, the cells were grown without any antibiotics, and allowed to form a monolayer.

Two methods were used to enrich for the population of cells expressing the antibacterial substance. It has been observed that antibacterial activity in cells expressing lytic peptides is associated with a loss of cellular sensitivity to trypsin. This trait allowed the selective removal of cells not expressing the antibacterial substance. Cultures demonstrating antibacterial activity were scraped to remove the trypsin-resistant cells. These trypsin-resistant cells were then further diluted and subcultured. Those cells continued to divide to produce a monolayer culture of FDD cells resistant to bacterial colonization. Cultures of cells expressing antibacterial activity were demonstrated to contain the cecropin gene by Southern blotting. Electroporated cell monolayers unable to prevent bacterial colonization were presumed to be negative for expression of the cecropin gene.

Pathogen Challenges

When the monolayer was complete, a first challenge with pathogenic *E. coli* (isolated from a case of equine cystiris) was added at a concentration of 10 bacteria/well. This low concentration was chosen to attempt to stimulate cecropin production, without overwhelming the culture. In the second challenge, bacteria were added at a rate of 1000/well and incubated overnight. After incubation, the wells were examined for colonization of the bacteria in clumps on the surface of the FDD cell monolayer. Bacterial colonization ranged from wells with no bacterial colonies to wells overgrown with bacterial colonies. Wells in which there was no colonization or only slight colonization (about 15% of the total) were rinsed, and antibiotic medium was added back to the wells. Cells were harvested and transferred to flasks to allow monolayer formation. It was observed that the FDD cultures which prevented colonization of bacteria also showed a loss of trypsin sensitivity. This same phenotypic trait had previously been observed in FDD cells following exposure to exogenous cecropin analogs.

The transformed FDD cells expressed the cecropin gene inductively, rather than constitutively. When the cells were split before exposure to bacteria, they were susceptible to treatment with trypsin; but after exposure to bacteria and subsequent cecropin production, the cells were resistant to trypsinization.

FDD cells positive and negative for antibacterial activity were expanded in 75 cm$^2$ flasks. Both groups of cells were challenged with $10^3$–$10^5$ EIA viral particles and incubated at 37° C. Daily examination of the cells showed the negative control cells acting as normally-infected EIA cells. However, the FDD cells positive for antibacterial activity demonstrated an increased cytopathic effect, manifested approximately 3 days before that of the control cells. This increased cytopathic effect is believed to be due to cecropin production by the FDD cells. These results demonstrate the usefulness of the present invention in treating virally-infected cells.

Electroporation of FDD cells has been repeated five times, and bacterial challenges have been performed on all five groups. Cells positive for antibacterial activity have been detected in each of the groups. Cells from the earliest electroporations have been passaged numerous times; they have also been frozen and brought back to culture; all without any apparent loss in viability or phenotypic changes. The incorporation of DNA appeared to be stable: cecropin mRNA was detected in cells descended from the first electroporation which had subsequently been passaged four times.

Confirmation of Transformation by Southern Blot

Southern blot analysis was performed both on FDD cells that were positive for antibacterial activity, and on FDD cells that were negative for antibacterial activity. Electroporated cells not receiving DNA were used as negative controls in the Southern analysis. The chromosomal DNA was harvested from FDD cells using the protocol of Ausubel et al., Current Protocols in Molecular Biology, vols. 1 and 2 (1991) for tissue-culture cells, and that DNA was electrophoresed on a 0.8% agarose gel. The DNA was transferred from the gel to a positively charged nylon membrane (Zeta Probe GT; Bio-Rad Laboratories, Richmond, Calif.), where it was probed with the cecropin gene isolated from pMON 200. The probe was prepared, and the subsequent hybridization was performed, using the non-isotopic Genius 1™ nonradioactive DNA labelling and detection kit (Boehringer Mannheim Corporation, Indianapolis, Ind.). The high stringency protocol was performed according to the manufacturer's instructions. Positive hybridization results were observed only in the electroporated cells receiving pCEP DNA, and in the pCEP vector used as a positive control. No hybridization was seen in the electroporated cells that did not receive pCEP DNA.

Confirmation of Transformation by PCR

FDD cells positive for cecropin were rinsed with PBS and fed with MEM which contained antibiotics as described above. The positive clones were passaged three times to try to insure that no cecropin or associated mRNA remained in the cells. After the third passage formed a monolayer, the cells were split into two groups. One group was challenged with bacteria, and the second group received a PBS treatment without bacteria as described above. After a 24-hour incubation, both groups were harvested, and RNA was harvested by the method of Ausubel et al., Current Protocols in Molecular Biology, vols. 1 and 2 (1991). Briefly, 3.5 ml of 4 M guanidinium thiocyanate solution was added per each $10^8$ cells, both to lyse the cells and to inactivate any RNase present. The resulting lysate was suspended in 5.7 M cesium chloride, and centrifuged at 150,000× g for 16 hours to separate RNA from DNA. The RNA pellet was resuspended in TES (10 mMTrisHCl, pH 7.4; 5 mM EDTA; 1% sodium dodecyl sulfate (SDS)), 3 M sodium acetate, and 100% ethanol, and then placed on dry ice/ethanol for 30 min to precipitate the RNA. The pelleted RNA was resuspended in 200 µL of sterile, distilled water, and quantitated by measuring absorbance at 260 nm and 280 nm.

The poly(A)–RNA (i.e., mRNA) was then separated from the tRNA and rRNA as follows. Total RNA was denatured by heating to 70° C. for 10 minutes to expose any poly(A)+ sites, and to disrupt secondary structures. The RNA mixture was passed through an oligo(dT) column to bind the poly(A)+ sites. The column was then washed twice to remove rRNA and tRNA, and then 2 mM EDTA/0.1% SDS was used to elute the mRNA. The mRNA was precipitated with ethanol and sodium acetate, and resuspended in TE (10 mM TrisHCl, pH 8.0, and 1 mM EDTA).

The mRNA was then used for PCR amplification using the semi-quantitative protocol of Dallman et al., "Semi-quantitative PCR for the analysis of gene expression," in Rickwood et al. (eds.), *PCR: A Practical Approach* (1991). Briefly, synthesis of cDNA from the mRNA was performed with reverse transcriptase from Moloney murine leukemia virus (Gibco-BRL). Using primers to the prececropin gene sequence, the cDNA was then amplified via PCR: cycle at 94° C., 1 min (denaturing); at 55° C., 2 min (annealing); and at 72° C. 1 min (extension). After 10–20 cycles, 15 µL samples can be taken at the end of every 5th cycle, and stored in 96-well microtiter plates. Quantitation of the unknown cDNA was achieved by having internal oligonucleotide standards that were titrated against the cDNA. The concentration of the standard at which the amount of amplification product was equal to the amount of amplification product from the target approximated the starting concentration of the experimental DNA (to within, say, an order of magnitude).

One group of transformed FDD cells was challenged with bacteria for 6 hours, after which the cells were harvested for mRNA isolation. Purified mRNA was reverse-transcribed to cDNA using Moloney Murine virus reverse transcriptase. Following the procedure described above, the cDNA was added to a PCR-amplification mixture with primers to pre-cecropin B, and was cycled 30 times in the thermocycler. FDD cells without vector DNA were used as negative controls. The mRNA from one group of cells showing antibacterial activity had a 180 bp fragment that corresponded to the size that was expected to be amplified, based on the design of the primers. This band was not present in the control cell mRNA, nor in the non-challenged cecropin-transformed FDD cells, showing that the cecropin was not constitutively produced.

Construction of Plasmid pCEP, and Transfection of E. coli with pCEP

The plasmid pCEP is a pBR322 derivative that carries the gene for ampicillin resistance and the ColE1 origin of replication, but in which a segment from base pair 105 to base pair 2345 has been deleted to streamline the plasmid, to allow incorporation of the native cecropin promoter and gene. The cecropin gene segment is the 5.9 Kb fragment isolated from the vector pMON 200 by a restriction digest with EcoR I and Xho I. Both ends were filled to create a blunt-ended fragment, as were the ends of the pBR322 plasmid.

The native cecropin gene was ligated into the modified pBR322 vector to give a construct of 9.3 Kb, using a modification of Ausubel et al., Current Protocols in Molecular Biology, vols. 1 and 2 (1991); and Sambrook et al., *Molecular Cloning, A Laboratory Manual,* 2nd ed. (1989). The modification increases the chance of blunt-end fragment insertion into the plasmid. The resulting recombinant plasmid, designated pCEP, was then electroporated into *Escherichia coli* NM554 (Stratagene, La Jolla, Calif.) using a BioRad Gene Pulser electroplator, under conditions described by the manufacturer for *E. coli*. Electroporated bacteria were plated onto Brain-Heart Infusion (BHI) agar containing 50 µL/mL of ampicillin, and incubated at 37° C. overnight. Because the ptac promoter is not read unless induced, the potentially lethal lytic peptide gene may be maintained in *E. coli* without the danger that the peptide will kill the *E. coli*.

Colonies growing on the BHI/ampicillin plates were subcultured in BHI/ampicillin broth for plasmid screening (Qiagen, Chatsworth, Calif.) and freezing at −70° C. Plasmid preparations of the isolates were examined by agarose gel electrophoresis. A 1% gel was electrophoresed for 4 hours at 4 V/cm, stained with 0.4 µg/mL ethidium bromide for 10 min., and destained in distilled water for 30 min. A supercoiled plasmid DNA ladder (Sigma Chemical) was used as a DNA size reference; bands corresponding to ~9.3 Kb were removed from the agarose and purified using the Eluquick™ DNA Purification Kit protocol. Purified plasmid DNA was then electroporated back into competent *E. coli* NM554 and selected on BHI/ampicillin plates. Because *E. coli* NM554 is a plasmid-less strain, this additional purification-electroporation step insured that there was only one plasmid type per cell by eliminating pBR322-pBR322 self-ligated dimers. Confirmation of the pCEP plasmid was obtained by growing E. coli NM554 on BHI/ampicillin plates; making plasmid preparations; making restriction digests with BamH I to yield two fragments of 2.3 and 7.0 Kb; and Southern blotting of the restriction digest under very stringent conditions using the cecropin gene isolated from pMON 200 as a probe.

A sample of this transformed *E. coli* strain NM554 containing plasmid pCEP with the cecropin gene was deposited with the American Type Culture Collection (ATCC), 12301 Parklawn Drive, Rockville, Md. 20852 on Jun. 30, 1993, and was assigned ATCC Accession No. 69342. This deposit was made pursuant to a contract between ATCC and the assignee of this patent application, Board of Supervisors of Louisiana State University and Agricultural and Mechanical College. The contract with ATCC provides for the permanent and unrestricted availability of the progeny of this *E. coli* strain to the public on the issuance of the U.S. patent describing and identifying the deposit or the publication or the laying open to the public of any U.S. or foreign patent application, whichever comes first, and for availability of the progeny of this *E. coli* strain to one determined by the U.S. Commissioner of Patents and Trademarks to be entitled thereto under pertinent statutes and regulations. The assignee of the present application has agreed that if the *E. coli* strain on deposit should die or be lost or destroyed when cultivated under suitable conditions, it will be promptly replaced on notification with a viable culture of the same *E. coli* strain.

After confirmation of the pCEP plasmid was completed, a large scale plasmid isolation was performed. A 250 mL culture of the transformed *E. coli* was grown in BHI/ampicillin broth on a rotary shaker at 37° C. until an $A_{600}=0.4$ was obtained, at which time chloramphenicol was added to give a final concentration of 180 μg/mL before amplifying the plasmid. Shaking was continued overnight. After 24 hours, the pCEP DNA was harvested using the Qiagen plasmid isolation protocol (Qiagen, Chatsworth, Calif.) and column to obtain pure, high quantity (0.7 μg/μL) plasmid DNA. A restriction digest using Pst I was conducted on 20 μg of the pCEP DNA to linearize the DNA prior to electroporation into a mammalian cell line as described above. The enzyme Pst I was chosen because it linearizes the plasmid without cutting the cecropin gene.

The pCEP plasmid itself was constructed as follows. Plasmid pNK2859 containing Tn10 derivative 103 (obtained from Dr. Nancy Kleckner, Department of Biochemistry and Molecular Biology, Harvard University; see Kleckner et al., pp. 139–180 in Miller (ed.), *Methods in Enzymology*, vol. 204 (1991)) was digested with the enzyme BamH I. This digestion had the effect of removing the kanamycin antibiotic resistance marker, but leaving the insertion sequences flanking the kanamycin resistance gene intact. The digest resulted in two bands approximately 3.2 Kb and 1.6 Kb in size. A double digestion was performed on the pMON 200 vector with the enzymes EcoR I and Xho I, yielding fragments of approximately 6 Kb and 9.7 Kb. These two enzymes remove the native cecropin B gene intact from the pMON 200 vector in the 6 Kb fragment. The resulting fragments from the two digests were separated by agarose gel electrophoresis on a 1% gel run at 40 V for four hours. The 3.2 Kb fragment from the Tn10 vector, and the 6 Kb fragment from the pMON 200 vector were excised from the gels, and each was separated from the agarose using the Eluquick™ DNA Purification Kit (Schleicher and Schuell, Keene, N.H.). This method minimized DNA shearing, and allowed efficient recovery of the desired fragments.

The purified DNA fragments did not have complimentary ends, so a blunt-end ligation protocol was designed, based on modifications of Ausubel et al., Current Protocols in Molecular Biology, vols. 1 and 2 (1991); and Sambrook et al., *Molecular Cloning, A Laboratory Manual*, 2nd ed. (1989). Briefly, blunt end fragments were created using Klenow fragment and dNTP's (final concentration of 0.5 mM) at an incubation temperature of 30° C. for 15 min, followed by deactivation at 75° C. for 10 min. Both the cecropin fragment and the Tn10 vector fragment were extracted in phenol:chloroform; precipitated in isopropanol; and resuspended in 10 μL of TE buffer ( 10 mM Tris, 5 mM EDTA, pH 8.0). The cecropin fragment was then ligated onto the Tn10 vector fragment using T4 DNA ligase and 40% PEG (polyethylene glycol) according to Sambrook et al., *Molecular Cloning, A Laboratory Manual*, 2nd ed. (1989). PEG was used to enhance the ligation of blunt-ended fragments, and to minimize the formation of concatemers of the same DNA.

The ligation mixture was incubated overnight at 20° C. The following day DNA was extracted in phenol:chloroform; precipitated in isopropanol; and resuspended in 10 μL of sterile, distilled $H_2O$. *E. coli* NM554 (Stratagene, La Jolla, Calif.) was made competent for electroporation using the protocol of BioRad, Inc (BioRad Laboratories, Hercules, Calif.). Electroporation was conducted at 1.65 KV, 200 Ω, and 25 μF using $10^{10}$ cells of competent *E. coil*. Two electroporations were performed: (1) $10^{10}$ cells with 5 μL of the ligated cecropin/vector DNA, and (2) a negative control using $10^{10}$ cells with 5 μL of sterile, distilled $H_2O$. Each electroporation mixture was immediately placed in 1 mL of BHI (Brain Heart Infusion, Difco Inc.) broth at 37° C. for one hour to recover, and to begin expression of the ampicillin resistance marker. After the one-hour recovery period, 200 μL of each mixture was applied to an agar plate using the spread plate technique to cover the entire plate. *E. coli* receiving the ligated pCEP plasmid were plated onto BHI agar plates supplemented with 100 μg/mL of ampicillin, while the *E. coli* receiving the distilled $H_2O$ were plated both on BHI agar plates with ampicillin, and on BHI agar plates without ampicillin as controls. All plates were incubated overnight at 37° C. All colonies growing on the BHI/ampicillin agar plates were then grown in BHI/ampicillin broth, and frozen at −70° C.

Each colony was also screened for the presence of a plasmid of approximately 9.391 Kb: 5.99 Kb from the cecropin gene segment, plus 3.401 Kb from the vector DNA. When suitable candidates were identified, the potential pCEP-bearing *E. coli* were propagated in a 100 mL culture of BHI/ampicillin broth grown to an optical density of $A_{600}=0.4$, at which time chloramphenicol was added to a final concentration of 170 μg/mL. The cultures were allowed to continue shaking overnight at 37° C. for plasmid replication. The pCEP DNA was then harvested using a modified version of the Qiagen (Qiagen, Chatsworth, Calif.) protocol. Insertion of the cecropin B gene was confirmed using Southern blot analysis, with labelled cecropin gene as a probe. The nonisotopic Genius 1™ nonradioactive DNA labelling and detection Kit (Boehringer Mannheim) was used to perform the Southern analysis, and each step was conducted under stringent hybridization conditions. Isolates positive for the cecropin insert were then tested for the production of cecropin B as described above.

A streamlined native cecropin promoter-cecropin B peptide vector will also be made. The gene sequence obtained from the pMON 200 vector is rather cumbersome to work with, in that it is 6 Kb long. Using the published sequence and restriction map of cecropin B (Xanthopoulas et al., "The Structure of the gene for cecropin B, an antibacterial immune protein from *Hyalphora cecropia*," Eur. J. Biochem., vol. 172, pp. 371–376 (1988)) a construct will be made which includes the entire gene, and which is about 3.1 Kb, about half the size of the 6 Kb sequence. DNA from the pMON 200 vector will be partially digested with EcoR I and BamH I. The fragments will be separated on an agarose gel, and purified with the Eluquick™ DNA Purification Kit protocol as described above. These fragments will then be cloned into a pBR322-derived plasmid with polylinkers with either EcoR I- or BamH I-complementary ends to the digested fragment to insure proper orientation in the construct.

Creating a smaller delivery vehicle for the cecropin gene will aid in sequencing the gene in a host cell using nucleic acid amplification techniques such as the polymerase chain reaction ("PCR"). Primers can be synthesized that will amplify internal segments of the cecropin gene, or segments extending into the host genome, to determine both the orientation and location of the gene in the host chromosome. A smaller fragment will enable sequencing with less time and expense.

The complete disclosures of all references cited in this specification are hereby incorporated by reference.

We claim:

1. A transformed mammalian cell in vitro, wherein said mammalian cell comprises an exogenous gene encoding cecropin B; wherein said cecropin B gene is stably incorporated into a chromosome of said mammalian cell; and wherein the expression of said cecropin B gene is "induced in response to a pathogen of said transformed mammalian cell and is" controlled by an inducible cecropin B promoter identical to the cecropin B promoter contained in the pCEP plasmid of *E. coli* strain ATCC accession number 69342, or is controlled by an inducible promoter having the requlatory properties of the inducible cecropin B promoter contained in the pCEP plasmid of *E. coli* strain ATCC accession number 69342.

2. A cell as recited in claim 1, wherein said cell comprises a fetal donkey dermal cell.

3. A cell as recited in claim 1, wherein said cell comprises a human cell.

4. A cell as recited in claim 1, wherein said cell comprises a hematopoietic stem cell.

5. A cell as recited in claim 4, wherein said cell comprises a human hematopoietic stem cell.

6. A cell as recited in claim 1, wherein said cell comprises a tumor infiltrating lymphocyte.

7. A cell as recited in claim 6, wherein said cell comprises a human tumor infiltrating lymphocyte.

8. A cell as recited in claim 1, wherein said cell is the progeny of a cell produced by transforming a mammalian cell with plasmid pCEP or a restriction digest of plasmid pCEP in the presence of isopropyl-$\beta$-D-thiogalactopyranoside, wherein said plasmid pCEP is equivalent to the plasmid contained in the *E. coli* strain having ATCC accession number 69342, whereby incorporation of the cecropin B gene into the mammalian cell's genome is promoted.

* * * * *